United States Patent [19]

Jensen

[11] Patent Number: 5,133,821
[45] Date of Patent: Jul. 28, 1992

[54] METHOD FOR CONTOURING HYDROCOLLOID WOUND DRESSINGS

[76] Inventor: Ole R. Jensen, 646 Orangeburgh Rd., River Vale, N.J. 07675

[21] Appl. No.: 801,640

[22] Filed: Dec. 3, 1991

Related U.S. Application Data

[63] Continuation of Ser. No. 615,065, Nov. 19, 1990, abandoned.

[51] Int. Cl.⁵ ............................................. B32B 31/14
[52] U.S. Cl. .................................. 156/245; 156/247; 156/249; 156/323; 156/344; 602/54; 602/900; 604/336; 604/344
[58] Field of Search .............. 156/245, 247, 249, 323, 156/244.11, 244.12, 244.18, 244.23, 244.24, 344; 128/155, 156; 604/336, 344

[56] References Cited

U.S. PATENT DOCUMENTS

| | | | |
|---|---|---|---|
| 1,988,787 | 1/1935 | Fowler | 18/10 |
| 2,232,109 | 2/1941 | Gibbons | 18/53 |
| 2,862,846 | 12/1958 | Blackford et al. | 128/156 |
| 2,895,170 | 7/1959 | Carlile | 18/47.5 |
| 2,988,774 | 6/1961 | Hely | 18/2 |
| 3,327,708 | 6/1967 | Sokolowski | 128/156 |
| 3,339,546 | 9/1967 | Chen | 128/156 |
| 3,574,809 | 4/1971 | Fairbanks | 264/167 |
| 3,824,761 | 7/1974 | Wright | 53/41 |
| 4,191,723 | 3/1980 | Vargin et al. | 264/129 |
| 4,323,533 | 4/1982 | Bramhall | 264/145 |
| 4,340,557 | 7/1982 | Gross | 264/146 |
| 4,357,935 | 11/1982 | Frantzich et al. | 128/156 |
| 4,414,970 | 11/1983 | Berry | 128/156 |
| 4,538,603 | 9/1985 | Pawelchak et al. | 128/156 |
| 4,551,490 | 11/1985 | Doyle et al. | 524/22 |
| 4,556,441 | 12/1985 | Faasse | 156/249 |
| 4,693,858 | 9/1987 | Volke | 264/101 |
| 4,762,124 | 8/1988 | Kerch et al. | 128/156 |
| 4,867,748 | 9/1989 | Samuelsen | 604/344 |
| 4,867,821 | 9/1989 | Morgan | 128/156 |

*Primary Examiner*—Caleb Weston
*Attorney, Agent, or Firm*—Tilton, Fallon, Lungmus

[57] ABSTRACT

A method for making individual contoured wound dressings comprising: providing a supply of a thin release web (40); and protective release covering (32); removably attaching and contouring a substantially continuous strip of an adhesive material (26) between said thin release web (40) and protective release covering (32) forming a first laminate (46); transporting said first laminate (46) to a delaminating station (54) whereat said thin release web (40) is peeled from said first laminate (46); supplying an adhesive carrier (28); merging and laminating said adhesive carrier (28) to the exposed adhesive layer forming a second laminate (64); and transporting said second laminate (64) to and through a cutting Station (68) to be cut into individual wound dressings or bandages.

14 Claims, 4 Drawing Sheets

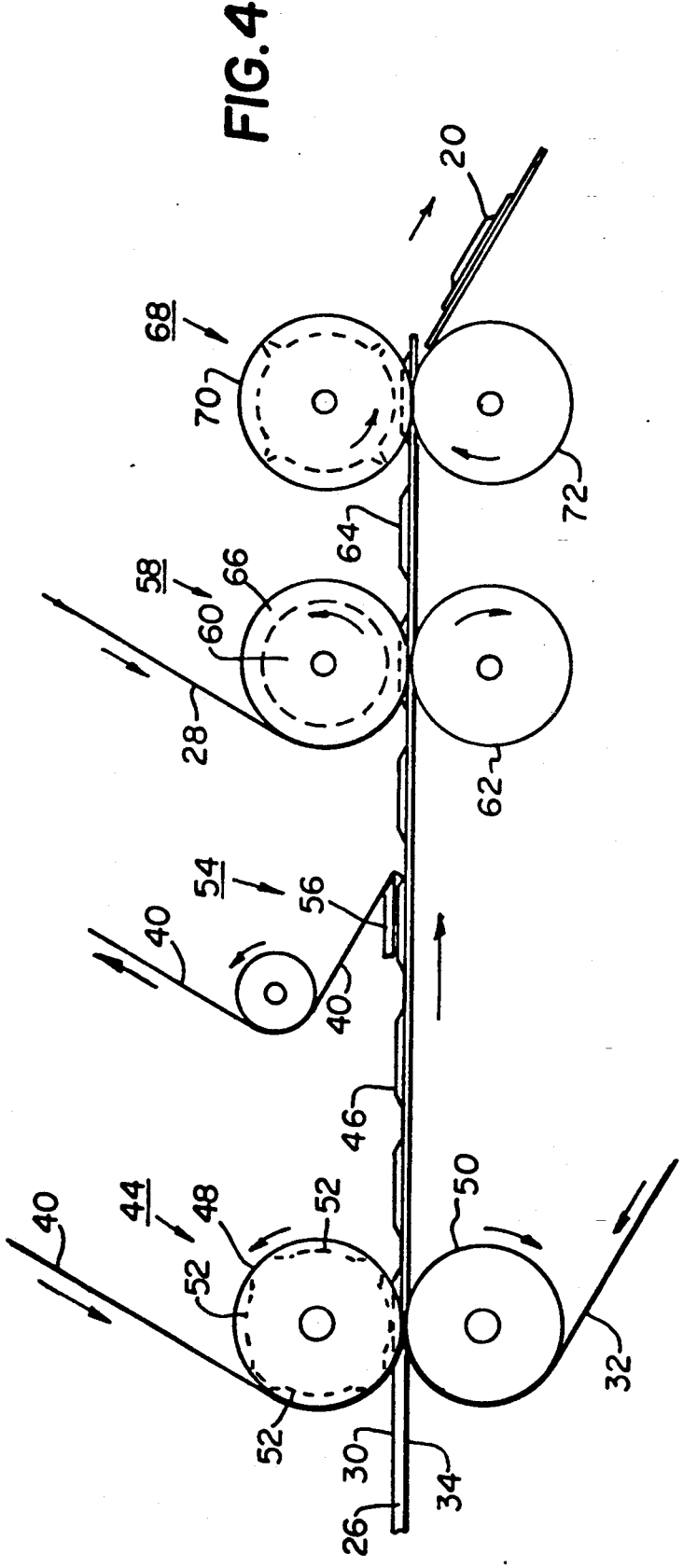
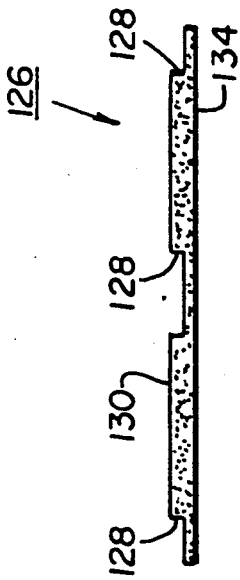
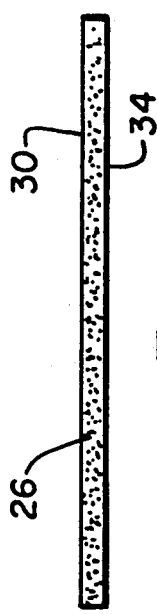

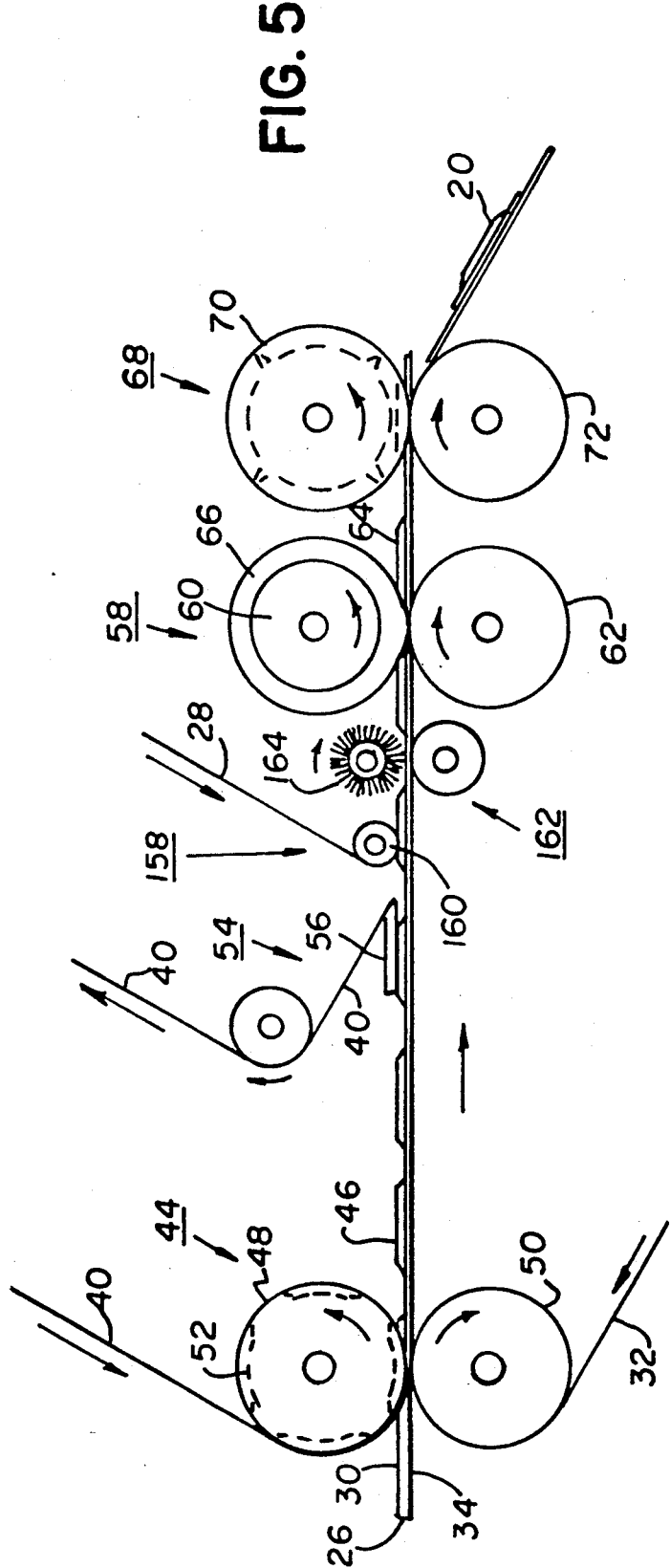

5,133,821

METHOD FOR CONTOURING HYDROCOLLOID WOUND DRESSINGS

RELATED APPLICATION

This application is a continuation of application Ser. No. 07/615,065, filed Nov. 19, 1990, abandoned.

BACKGROUND OF THE INVENTION

1. Field of the Invention

This invention is believed to be found in the field of methods for making contoured wound dressings or bandages, and more particularly a substantially continuous in-line method for contouring of a hydrocolloid wound dressing.

2. Description of the Prior Art

Methods of making wound dressings or bandages are discussed in U.S. Pat. No. 3,339,546 as issued to Chen on Sep. 5, 1967; U.S. Pat. No. 4,867,748, as issued to Samuelson on Sep. 19, 1989; and the applicants co-pending application Ser. No. 590,684, filed Oct. 1, 1990. Chen discusses a two step process comprising a roller mill step followed by a flat press step. Samuelson discusses a flat press method and/or a die casting method. The applicants co-pending application Ser. No. 590,684 mentions various possible methods for producing the disclosed wound dressing but does not present a detailed description of the methods.

It has been determined that there is a need to reduce the cost, time, and energy requirements to make a wound dressing which uses a skin-friendly adhesive layer. It can be seen that the methods disclosed by Chen in U.S. Pat. No. 3,339,546 and Samuelson in U.S. Pat. No. 4,867,748 consume a large amount of energy and may require a relatively long press cycle.

In the previously cited references and as far as it is known, an in-line, substantially continuous method for the contouring of a hydrocolloid type wound dressing or bandage has not been shown or disclosed.

The present invention will provide an economical method for producing a very desireable type of wound dressing, by performing the various operations of making a wound dressing in a substantially sequential and continuous manner. This method as taught in the present disclosure substantially reduces the energy requirements needed to make the wound dressing. It is believed that a reduction in energy requirements along with increased production output will significantly reduce the cost of making this highly desirable wound dressing.

SUMMARY OF THE INVENTION

This invention may be summarized, at least in part, with respect to its objects.

It is an object of this invention to provide and it does provide a method for making a hydrocolloid wound dressing or bandage in a substantially continuous and sequential manner.

It is another object of this invention to provide and it does provide a method for making a hydrocolloid wound dressing or bandage which substantially reduces the energy and the time required to selectively contour the wound dressing or bandage.

It is yet another object of this invention to provide and it does provide a substantially in-line process for making a contoured hydrocolloid adhesive wound dressing or bandage.

It is still yet an object of this invention to provide and it does provide a method for making a contoured wound dressing or bandage which is cost effective.

It is still yet another object of this invention to provide and it does provide a method for continuously making a contoured wound dressing which substantially eliminates any and all air pockets between laminated layers of the dressing.

In addition to the above summary, the following disclosure is detailed to insure adequacy and aid in the understanding of this invention. This disclosure, however, is not intended to cover each new and inventive concept, no matter how it may later be disguised either by variations in form or addition by further improvements. For this reason, there has been chosen specific embodiments of a method for contouring a hydrocolloid adhesive wound dressing or bandage. These specific embodiments have been chosen for the purpose of illustration and description, as shown in the accompanying drawing wherein:

BRIEF DESCRIPTION OF THE DRAWING

FIG. 4 represents one embodiment of the present invention, partly diagrammatic and partly schematic.

FIG. 5 represents an alternate embodiment of the present invention, this view partly diagrammatic and partly schematic.

FIG. 7 represents a sectional view of a hydrocolloid adhesive layer prior to entering a first operational station of the present invention.

FIG. 8 represents a sectional view of an alternate profile for the hydrocolloid adhesive prior to the first operational station of the present invention.

In the following description and claims, various details are identified by specific names for convenience. These names are intended to be substantially generic in their application. The corresponding reference characters refer to like members throughout the several figures of the drawings.

The drawings, accompanying and forming a part of this specification, disclose certain details associated with the method of contouring the adhesive layer of a wound dressing or bandage. These details are for the purpose of explanation, but it is understood that some details my be modified without departure from the concept and principles of the present invention. It is anticipated that this invention may also be incorporated in forms other than shown or described.

EMBODIMENT OF FIG. 1; FIG. 2; AND FIG. 3

Figure 1:
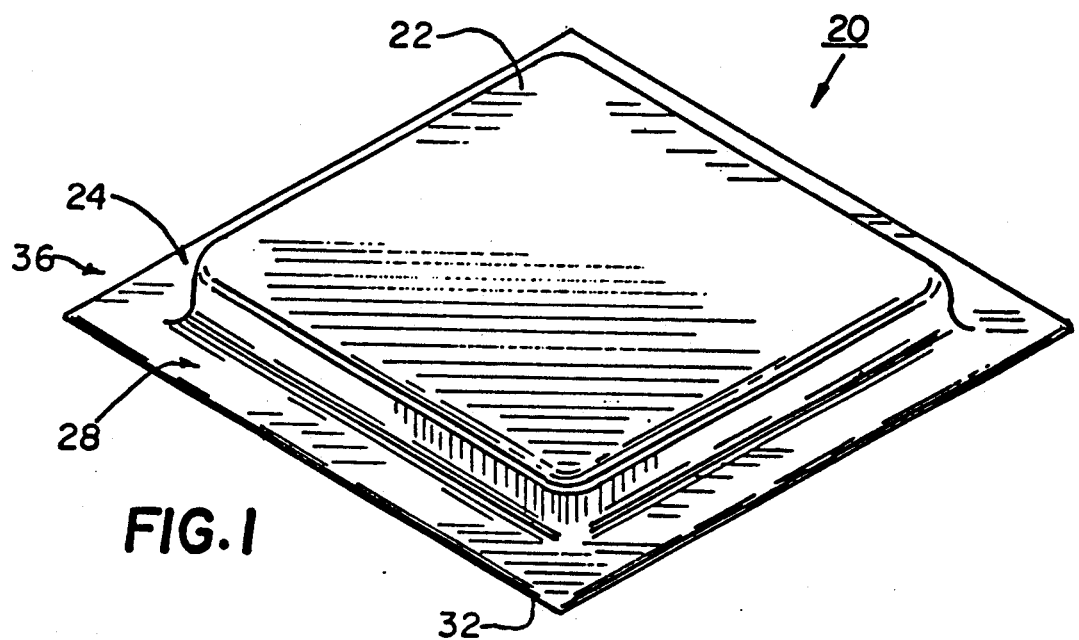
FIG. 1 represents an isometric view of one type of a wound dressing that may be made by using the method of the present invention.

Referring to FIG. 1, an individual wound dressing or bandage, generally identified as 20, is representative of one of the end products that may be made by using the method of the present invention. This dressing 20 has a thick absorbent portion 22 and a thin flange portion 24.

Figure 2:
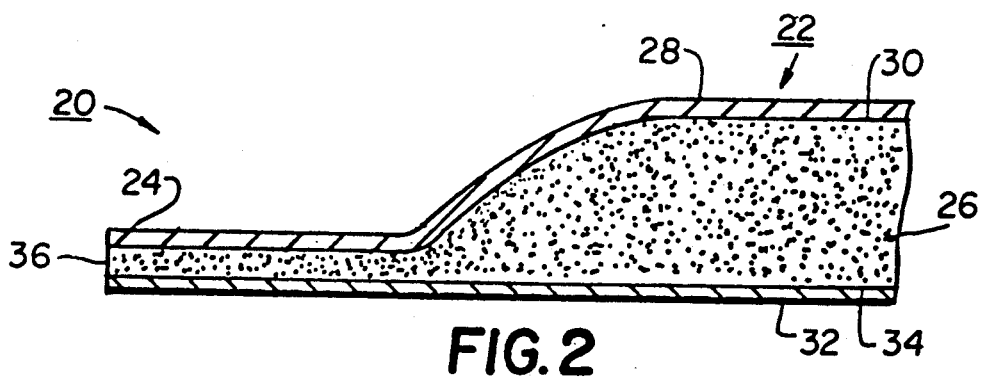
FIG. 2 represents a fragmentary view, in section and in an enlarged scale, of one type of contoured adhesive layer that may be made by using the method of the present invention.

Referring now to FIG. 2, there is shown an enlarged fragmentary cross-sectional view of the dressing or bandage 20. The dressing 20 has a contoured adhesive layer 26 which has an adhesive carrier layer 28 fully attached to a first major surface 30 of the adhesive layer 26 and a protective release covering 32 is removably attached to a second major surface 34.

Figure 3:
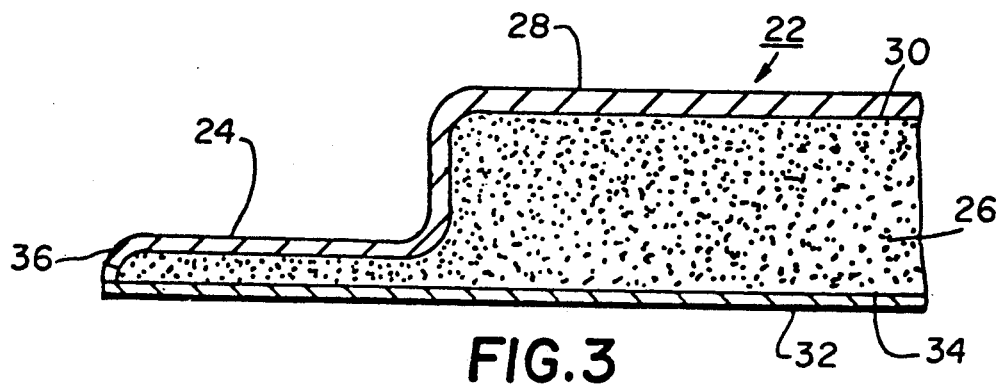
FIG. 3 represents a fragmentary view, in section and in the scale of FIG. 2, of an alternate embodiment of the contoured portion of the adhesive layer that may be made by the method of the present invention.

Referring to FIG. 3, an alternate arrangement for the dressing 20 is shown. This alternate arrangement provides for the complete covering of the adhesive layer 26 by the adhesive carrier layer 28, more particularly a tip portion 36 of the thin flange portion 24 is fully protected by and with the adhesive carrier layer 28.

The embodiments of FIG. 1; FIG. 2; and FIG. 3 are presented to show some of the types of bandages that may be made by the method of the present invention. This invention may be used to make any of the wound dressings or bandages shown and described in the applicants co-pending application Ser. No. 590,684 referenced above but not limited thereto. Co-pending application Ser. No. 590,684 is incorporated into this specification by reference to the extent allowed by law. The present invention may also be used to make the dressing as shown and disclosed in U.S. Pat. No. 4,867,748 as issued to Samuelson.

EMBODIMENT OF FIG. 4

Referring now to FIG. 4, one embodiment of the present invention is diagrammatically and schematically shown. A substantially continuous web of a thin release material 40 is provided from a first supply roll, not shown. A substantially continuous web of a thin protective release covering 32 is supplied from a second roll of material, not shown. The thin release web 40 and protective release covering 32 are delivered to and are carried through a calibration and contouring station 44 at a selected rate. This contouring station 44 contours at least one of the major surfaces 30 or 34 of a substantially continuous strip of a hydrocolloid adhesive 26.

This continuous strip of hydrocolloid adhesive 26 having predetermined malleable properties is delivered between the thin release web 40 and thin protective release covering 32. A first laminate 46 comprising said said adhesive layer 26; interposed between the thin release web 40 and thin protective release covering 32 is contoured by the co-operating rotational action of a first contouring roller 48 and a second contouring roller 50. The first contouring roller 48 has been relieved along its peripheral surface to provide shaped pockets 52. The pockets 52 are shaped substantially as the desired final contour of the dressing or bandage 20. The thin release web 40 is made of a material having a release coating on at least one of its surfaces. It is preferred that the thin release web 40 be of a silicone release paper with its treated or release side facing and contacting the adhesive layer 26. The thin release web 40 provides a means for allowing the first major surface 30 of the adhesive layer 26 to be contoured without any transfer of Hydrocolloid adhesive to the first contouring roller 48. The thin release web 40 also minimizes the friction generated during the contouring of the adhesive 26 by the action of the rollers 50 and 52.

The contoured first laminate 46 is transported in a substantially continuous manner to a subsequent delaminating station 54. The thin release web 40 is separated from the first lamination 46 and transported to a collection means, not shown. A selectively shaped stripper plate 56 provides the desired delamination or separation of the thin release web 40 from the adhesive layer 26 thereby exposing a contoured first major surface 30 of the adhesive layer 26.

The adhesive layer 26 carried on the thin protective release covering 32 continues to be transported to a laminating station 58 where-at an adhesive carrier layer 28 is merged with the transported laminate of an adhesive layer 26 and the protective release covering 32. The adhesive carrier layer 28 is of a water impermeable type but other suitable materials may be used. It is also very thin and easily conforms to the contour of the exposed first major surface 30. A first laminating roller 60 and a second laminating roller 62 cooperate to form a second laminate 64. This second laminate 64 comprising the adhesive carrier 28; interposed between the adhesive layer 26; and the protective release covering 32 is transported in a substantially continuous manner towards a subsequent station.

The first laminating roller 62 has an outer rubber layer 66, preferably a silicone rubber or foam rubber but other suitable coverings may be used. This outer rubber layer 66 provides a complete covering and attaching of the adhesive layer 26 by and with the adhesive carrier layer 28 without substantially altering the contour of the dressing 20. This second laminate 64 is substantially free of any air pockets between the layers.

The first laminate 46 and second laminate 64 are transported to and through a cutting station 68. The first cutting roller 70 and second cutting roller 72 are rotated at a selected speed to cut the second laminate 64 into individual or discrete wound dressings or bandages 20. These individual wound dressings or bandages 20 are delivered to a collection site or to a subsequent packaging operation.

The rollers of the laminating station 58 provide a drive means for transporting the continuous lamination of layers of the dressing through the various operating stations. The die cutting station 68; laminating station 58; and calibration and contouring station 44 are rotated in a timed and synchronized relationship to each other to provide the desired spacing and contours between the dressings. This timed relationship may be provided mechanically, electro-mechanically, electronically or by other suitable means. The individual stations should be individually adjustable with respect to the spacing between each pair of associated rollers to provide or compensate for the desired thickness of the wound dressing.

EMBODIMENT OF FIG. 5

Referring now to FIG. 5, there is shown an alternative embodiment for making the wound dressing or bandage 20. This alternative embodiment comprises a calibration and contouring station 44 where-at a first laminate 46 is contoured as desired. As in FIG. 4 this first laminate comprises an adhesive layer 26 interposed between a thin release layer 40 and a protective release covering 32. This first laminate 46 is transported in a substantially continuous manner towards a delaminating station 54 where-at the thin release web 40 is peeled or separated from the first laminate 46 by way of stripper plate 56. The resultant laminate with its major surface 30 exposed is transported to merging station 158 which comprises a change of direction roller 160 which merges the adhesive carrier layer 28 onto the exposed major surface 30 of the adhesive layer 26.

The second laminate 64 comprising a contoured adhesive layer 26, interposed between the adhesive carrier layer 28, and the protective release covering 32 is then brought to an air removing station 162. This air removing station 162 provides a rotating brush 164 which applies the adhesive carrier layer 28 to the contoured adhesive layer 26. The action of the rotary brush 164 removes substantially all of the air pockets that may become entrapped between the adhesive carrier layer 28 and the contoured adhesive layer 28. This removal of substantially all of the air pockets eliminates any dry spots on and in the adhesive layer.

The second laminate 64 is then brought to and through a laminating station 58 where-at further pressure is applied to marry the adhesive carrier 28 to the adhesive 26. The method from this point to the collection of the individual bandages is substantially identical to that as described above in FIG. 4.

EMBODIMENT OF FIG. 6

Figure 6:
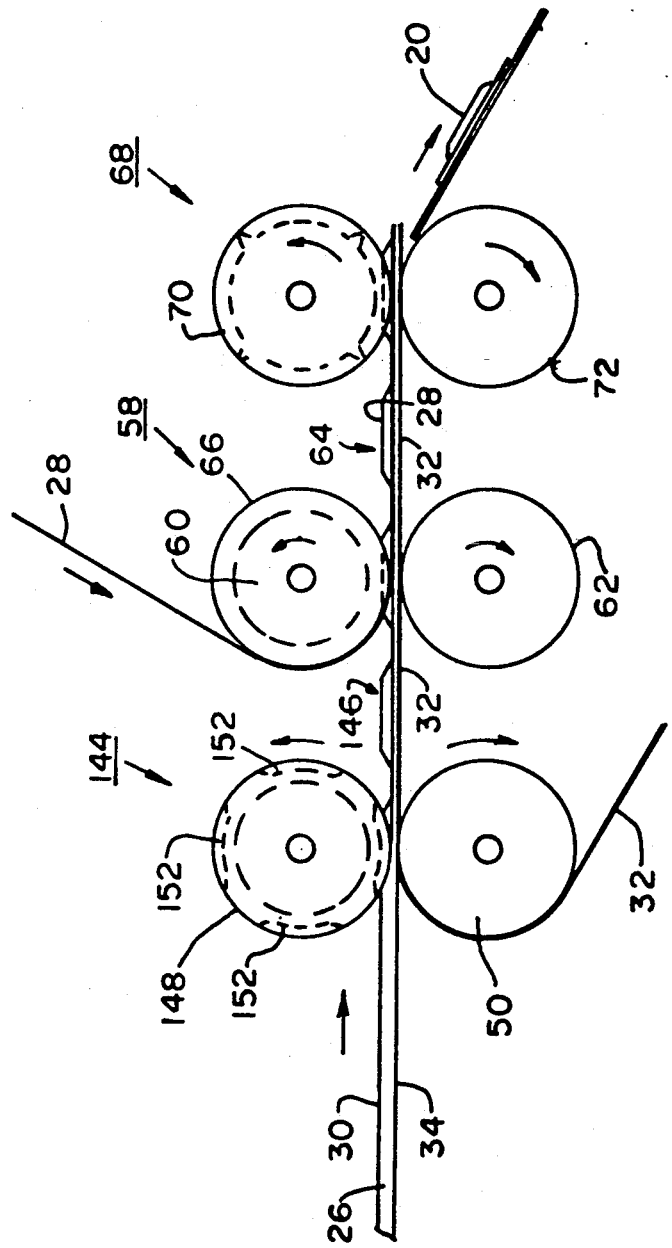
FIG. 6 represents a second alternate embodiment of the method of the present invention, this view being partly diagrammatic and partly schematic.

Referring now to FIG. 6, there is shown a second alternate embodiment for making the wound dressing or bandage 20. This second alternate embodiment also provides delivery of a substantially continuous strip of a hydrocolloid adhesive 26 to a calibration and contouring station 144. A substantially continuous supply of a protective release covering 32 is laminated to said adhesive layer 26 forming a first laminate 146. This laminate 146 is selectively contoured by the co-operating rotational action of a first contouring roller 148 and a second contouring roller 50. The first contouring roller 148 has been relieved along its peripheral surface to provide a plurality of shaped pockets 152. In this second embodiment, the first contouring roller 148 has its entire peripheral surface including its pockets 152 coated with a release coating such as a silicone rubber or Teflon ®.

The coating of the first contouring roller with a release material aids in reducing the friction between the roller 148 and the adhesive layer 26 and insures that none of the adhesive 26 will collect on the roller 148. The first laminate 146 is then carried to a subsequent laminating station 58 and a cutting station 68. It is to be noted that this first laminate 146 may be transported through a merging station 158 and an air removal station 162 if found to be required. The operation of the subsequent stations 58, 68, 158, and 162 have been previously described above in FIG. 4 and FIG. 5.

EMBODIMENT OF FIG. 7 AND FIG. 8

Referring to FIG. 7, there is shown a cross-sectional profile of a strip of adhesive 26 as it is delivered to the calibration and contouring station. This strip 26 has a substantially uniform cross-section having a predetermined thickness and width.

Referring now to FIG. 8, an alternative profile for a strip of adhesive 126 is shown as it may be delivered to the calibration and contouring station 44. The strip of adhesive 126 may be extruded with rows of ridges 128 formed into at least one of its major surfaces 30 or 34. These rows of ridges 128 are aligned with those portions of the roller 48 which form the two longitudinal thin flange portions 24 of the wound dressing 20. It can be seen that this preparatory profiling as shown in FIG. 8, will substantially reduce the forces necessary for the displacement of the adhesive layer as it is transported through the calibration and contouring station 44.

The previous description has primarily described a wound dressing or bandage with one contoured side. The method as disclosed above, may also be used to make a wound dressing which has both of its major surfaces contoured. Of course the rollers 50, 62, and 72 must be selectively relieved or undercut to provide the desired contours.

It has been found that the method as disclosed and shown in FIG. 4 makes wound dressings having a thick absorbent portion 22 within the range between 0.75 mm. and 2.0 mm. and a thin flange portion 24 within the range between 0.10 mm and 0.30 mm. The contouring of both major surfaces 30 and 34 may be necessary when it is required that a thick absorbent portion 22 have a thickness greater than 2.0 mm.

It is to be noted that rollers 48, 60, and 70 may have a staggered pattern along their peripheral surfaces to minimize the contouring force required at any radial point along the peripheral surface. The choice of the patterns in and on the rollers is a matter of design selection.

The methods as shown and described above may be used in contouring known hydrocolloids or other dough-like adhesives. These methods may be used to form a single or multiple rows of wound dressings. The only limitation is the length of the rollers associated with this method and the capacity of the machinery.

It is believed that the above description and drawing provides the basis for the method of making a contoured hydrocolloid adhesive dressing comprising the following steps:

providing a substantially continuous supply of a thin release web of material;

providing a substantially continuous supply of a thin protective release covering;

providing a substantially continuous strip of a hydrocolloid adhesive, said adhesive having selectively predetermined malleable properties;

removably attaching said strip of adhesive between said thin release web and said protective release covering while simultaneously contouring said adhesive material by and with a calibration and contouring station;

exposing a major surface of said contoured adhesive material by removing said thin release web from said contoured adhesive by and with a delaminating station;

providing a substantially continuous web of an adhesive carrier material;

merging said adhesive carrier layer with said exposed adhesive layer by a merging station;

removing substantially any and all gas pockets between said adhesive material and said adhesive carrier layer by an air removing station;

applying a pressure to a second laminate by carrying said laminated through a laminating station;

cutting said laminate into descrete and individual sized wound dressing by a cutting station; and collecting said individual bandages.

Terms such as "left", "right", "up", "down", "bottom", "top", "front", "back", "in", "out", and the like are applicable to the embodiments shown and described in conjunction with the drawings. These terms are merely for the purpose of description and do not necessarily apply to the position in which the method of the present invention may be utilized.

While these particular embodiments of an improved method has been shown and described, it is to be understood that the invention is not limited thereto and protection is sought to the broadest extent the prior art allows.

What is claimed is:

1. A method for making discrete and individual wound dressings having a contoured skin-friendly and moisture activated adhesive layer, said method including the following steps;
   (a) providing a substantially continuous supply of a thin release web of material;
   (b) providing a substantially continuous supply of a thin protective release covering;
   (c) providing a substantially continuous strip of an adhesive material, said strip of adhesive having predetermined thickness and malleable properties;
   (d) removably attaching said strip of adhesive material to and between said thin release web and said protective release covering while simultaneously contouring said adhesive material to a predetermined shape by merging and carrying a first laminate of said adhesive material, thin release web and said protective release covering through a calibration and contouring station;
   (e) exposing a major surface of said contoured adhesive material by removing said thin release web from said contoured adhesive material by carrying said first laminate to and through a subsequent delaminating station;
   (f) providing a substantially continuous web of an adhesive carrier material;
   (g) merging said adhesive carrier layer with said contoured adhesive layer to form a second laminate by applying said adhesive carrier layer to fully cover said exposed major surface of said adhesive layer while simultaneously applying pressure to said second laminate by carrying said second laminate to and through a laminating station; and
   (h) cutting said second laminate into predetermined discrete sized and contoured individual wound dressings by carrying said second laminate to and through a cutting station in a predetermined registered and timed relationship.

2. A method as recited in claim 1 wherein the step of carrying said second laminate to and through said laminating station further includes:
   simultaneously removing any and all gas pockets interior of said second laminate by and with said laminating station.

3. A method for making discrete and individual wound dressings having a contoured skin-friendly and moisture activated adhesive layer, said method including the following steps:
   (a) providing a substantially continuous supply of a thin release web of material;
   (b) providing a substantially continuous supply of a thin protective release covering;
   (c) providing a substantially continuous strip of an adhesive material, said strip of adhesive having predetermined thickness and malleable properties;
   (d) removably attaching said strip of adhesive material to and between said thin release web and said protective release covering while simultaneously contouring said adhesive material to a predetermined shape by merging and carrying a first laminate of said adhesive material, thin release web and said protective release covering through a calibration and contouring station;
   (e) exposing a major surface of said contoured adhesive material by removing said thin release web from said contoured adhesive material by carrying said first laminate to and through a subsequent delaminating station;
   (f) providing a substantially continuous web of an adhesive carrier material;
   (g) merging said adhesive carrier layer with said contoured adhesive layer to form a second laminate by applying said adhesive carrier layer to cover said exposed major surface of said adhesive layer at a merging station;
   (h) removing substantially any and all gas pockets interior of said second laminate by carrying said second laminate through a air removing station;
   (i) applying pressure to said second laminate by carrying said second laminate to and through a laminating station; and
   (j) cutting said second laminate into predetermined discrete sized and contoured individual wound dressings by carrying said second laminate to and through a cutting station in a predetermined registered and timed relationship.

4. A method for making discrete and individual wound dressings having a contoured skin-friendly and moisture activated adhesive layer, said method including the following steps;
   (a) providing a substantially continuous supply of a thin protective release covering;
   (b) providing a substantially continuous strip of an adhesive material, said strip of adhesive having predetermined thickness and malleable properties;
   (c) removably attaching said strip of adhesive material to said protective release covering while simultaneously contouring said adhesive material to a predetermined shape by merging and carrying a first laminate of said adhesive material, and said protective release covering through a calibration and contouring station;
   (d) providing a substantially continuous web of an adhesive carrier material;
   (e) merging said adhesive carrier layer with said contoured adhesive layer to form a second laminate by applying said adhesive carrier layer to fully cover said exposed major surface of said adhesive layer while simultaneously applying pressure to said second laminate by carrying said second laminate to and through a laminating station; and
   (f) cutting said second laminate into predetermined discrete sized and contoured individual wound dressings by carrying said second laminate to and through a cutting station in a predetermined registered and timed relationship.

5. A method as recited in claims 1, 3, or 4 wherein the step of providing a continuous strip of an adhesive material includes the further steps:
   mixing a selected formulation of a skin friendly and moisture activated adhesive; and
   selectively shaping said formulated adhesive into said continuous strip.

6. A method as recited in claim 5 wherein said step of selectively shaping said adhesive strip includes forming a plurality of elongated rows of ridged surfaces in and on at least one of a first major surface and a second major surface of said adhesive strip.

7. A method as recited in claim 5 wherein said mixing further includes formulating a hydrocolloid adhesive material.

8. A method as recited in claim 6 wherein said mixing further includes formulating a hydrocolloid adhesive material.

9. A method as recited in claims 1, 3, or 4 including the further step of collecting said individual wound dressings subsequent to said cutting.

10. A method as recited in claims 1, 3, or 4 wherein said carrying the first laminate through a calibration and contouring station includes selectively rotating a first contouring roller and a second contouring roller; and providing at least one of said first contouring roller and said second contouring roller with a selectively contoured peripheral surface.

11. A method as recited in claims 1, 3, or 4 including the further step of operating said calibration and contouring station, said laminating station, and said cutting station in a selectively synchronized and timed relationship.

12. A method as recited in claim 10 wherein said carrying of said second laminate to and through a laminating station includes selectively rotating a first laminating roller and a second laminating roller; and providing at least one of said first laminating roller and said second laminating roller with a selectively resilient peripheral surface.

13. A method as recited in claim 12 wherein said carrying said second laminate to and through a cutting station further includes selectively rotating a first cutting roller and a second cutting roller; and providing at least one of said first cutting roller and said second cutting roller with a selectively contoured peripheral cutting surface.

14. A method as recited in claim 3 wherein the step of removing gas pockets includes rotating at least one rotary brush.

* * * * *